US007901689B2

(12) United States Patent
Chain

(10) Patent No.: US 7,901,689 B2
(45) Date of Patent: Mar. 8, 2011

(54) CHIMERIC PEPTIDES AS IMMUNOGENS, ANTIBODIES THERETO, AND METHODS FOR IMMUNIZATION USING CHIMERIC PEPTIDES OR ANTIBODIES

(75) Inventor: Benjamin Chain, London (GB)

(73) Assignee: Intellect Neurosciences, Inc., New York, NY (US)

( * ) Notice: Subject to any disclaimer, the term of this patent is extended or adjusted under 35 U.S.C. 154(b) by 2708 days.

(21) Appl. No.: 09/731,899

(22) Filed: Dec. 8, 2000

(65) Prior Publication Data

US 2006/0088548 A1 Apr. 27, 2006

Related U.S. Application Data

(60) Provisional application No. 60/169,687, filed on Dec. 8, 1999.

(51) Int. Cl.
*A61K 39/00* (2006.01)
*A61K 49/00* (2006.01)
*A61K 39/05* (2006.01)

(52) U.S. Cl. ..... 424/185.1; 424/9.1; 424/9.2; 424/184.1; 424/190.1; 424/192.1; 424/193.1; 424/234.1; 424/236.1; 424/245.1; 530/300; 530/350

(58) Field of Classification Search ................... 424/9.1, 424/9.2, 184.1, 185.1, 190.1, 192.1, 193.1, 424/234.1, 236.1, 245.1; 530/300, 350
See application file for complete search history.

(56) References Cited

U.S. PATENT DOCUMENTS 5,879,909 A * 3/1999 Perl .............................. 435/69.1

FOREIGN PATENT DOCUMENTS

| WO | WO98/23635 | * | 6/1998 |
|----|------------|---|--------|
| WO | 98/44955 A1 | | 10/1998 |
| WO | WO 99/27944 A1 | | 6/1999 |
| WO | WO-00/72876 A2 | | 12/2000 |
| WO | WO 00/72880 A2 | | 12/2000 |

OTHER PUBLICATIONS

Schenk et al., "Immunization with amyloid-β attenuates Alzheimer-disease-like pathology in the PDAPP mouse", Nature, 400.173 177 (Jul. 1999).
Sharma et al., "Co-dominant and reciprocal T-helper cell activity of epitopic sequences and formation of junctional B-cell determinants in synthetic T:B chimeric immunogens", Vaccine, 11:1321-1326 (1993).
Ifversen et al., "Induction of primary antigen-specific immune responses in SCID-hu-PBL by coupled T-B epitopes", Immunology, 84:111-116 (1995).
O'Hern et al., "Colinear synthesis of an antigen-specific B-cell epitope with a 'promiscuous' tetanus toxin T-cell epitope: a synthetic peptide immunocontraceptive", Vaccine, 16:1761-1766 (1997).
Ho et al., "Identification of two promiscuous T cell epitopes from tetanus toxin", Eur. J. Immunol., 20:477-483 (1990).
Panina-Bordignon et al., "University immunogenic T cell epitopes: promiscuous binding to human MHC class II and promiscuous recognition by T cells", Eur. J. Immunol., 19:2237-2242 (1989).
Valmori et al., "Use of human universally antigenic tetanus toxin T cell epitopes as carriers for human vaccination", The Journal of Immunology, 149:717-721 (Jul. 15, 1992).
Valmori et al., "Functional analysis of two tetanus toxin universal T cell epitopes in their interaction with DR1101 and DR1104 alleles", Journal of Immunology, 2921-2929 (1994).
Schofield et al., "Sequences of the mouse F protein alleles and identification of a T cell epitope", Eur. J. Immunol., 21:1235-1240 (1991).
Talwar et al., "The HSD-hCG vaccine prevents pregnancy in women: feasibility study of a reversible safe contraceptive vaccine", American Journal of Reproductive Immunology, 37:153-160 (1997).
Iwatsubo et al., "Short communication full-length amyloid-β(1-42(43)) and amino-terminally modified and truncated amyloid-β42(43) deposit in diffuse plaques", American Journal of Pathology, 149:1823-1830 (Dec. 1996).
Brons et al, "Hierarchic T-Cell Help to Non-Linked B-Cell Epitopes", Scand J Immunol 44:478-484 (1996).
Delmas et al, "The binding of chimeric peptides to GM1 ganglioside enables induction of antibody responses after intranasal immunization" Vaccine 14(11):1077-1082 (1996).
Frenkel et al, "N-terminal EFRH sequence of Alzheimer's β-amylold peptide represents the epitope of its anti-aggreating antibodies", J Neuroimmunology 88:85-90 (1998).
Partidos et al, "The influence of orientation and number of copies of T and B cell epitopes on the specificity and affinity of antibodies induced by chimeric peptides", Eur J Immunol 22:2675-2680 (1992).
Saido et al., "Amino- and carboxyl-terminal heterogeneity of beta-amyloid peptides deposited in human brain,"Neurosience Letters 215:173-176 (1996).

* cited by examiner

Primary Examiner — Rodney P. Swartz
(74) Attorney, Agent, or Firm — Fish & Richardson P.C.

(57) ABSTRACT

The invention provides a chimeric peptide or mixture of chimeric peptides that can be formulated as an immunizing composition and used in a method for immunization of a mammal against an internal peptide cleavage product derived from a precursor or mature protein, for which the peptide cleavage product and the precursor or mature protein are self molecules. The chimeric peptide or peptides have an end-specific B cell epitope from a naturally-occurring internal peptide cleavage product of a precursor or mature protein, as a free N- or C-terminus, fused with or without spacer residues to a T helper cell epitope derived from a living source different from that of the internal peptide cleavage product.

25 Claims, 2 Drawing Sheets

SEQUENCE LISTING

<160> NUMBER OF SEQ ID NOS: 27

<210> SEQ ID NO 1
<211> LENGTH: 59
<212> TYPE: PRT
<213> ORGANISM: Homo sapiens

<400> SEQUENCE: 1

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45

Ile Val Ile Thr Leu Val Met Leu Lys Lys Lys
    50                  55

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is L-Asp, D-Asp, or L-iso Asp

<400> SEQUENCE: 3

Xaa Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 43
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

```
<210> SEQ ID NO 5
<211> LENGTH: 40
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is pyroglutamate

<400> SEQUENCE: 5

Xaa Phe Arg His Asp Ser Gly Tyr Glu Val His His Gln Lys Leu Val
 1               5                  10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 6
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is pyroglutamate

<400> SEQUENCE: 6

Xaa Val His His Gln Lys Leu Val Phe Phe Ala Glu Asp Val Gly Ser
 1               5                  10                  15

Asn Lys Gly Ala Ile Ile Gly Leu Met Val Gly Gly Val Val Ile Ala
            20                  25                  30

<210> SEQ ID NO 7
<211> LENGTH: 26
<212> TYPE: PRT
<213> ORGANISM: Homo sapiens

<400> SEQUENCE: 7

Leu Val Phe Phe Ala Glu Asp Val Gly Ser Asn Lys Gly Ala Ile Ile
 1               5                  10                  15

Gly Leu Met Val Gly Gly Val Val Ile Ala
            20                  25

<210> SEQ ID NO 8
<211> LENGTH: 14
<212> TYPE: PRT
<213> ORGANISM: Tetanus toxin bacteria

<400> SEQUENCE: 8

Gln Tyr Ile Lys Ala Asn Ser Lys Phe Ile Gly Ile Thr Glu
 1               5                  10

<210> SEQ ID NO 9
<211> LENGTH: 15
<212> TYPE: PRT
<213> ORGANISM: Hepatitis B virus

<400> SEQUENCE: 9

Phe Phe Leu Leu Thr Arg Ile Leu Thr Ile Phe Gln Ser Leu Asp
 1               5                  10                  15

<210> SEQ ID NO 10
<211> LENGTH: 30
<212> TYPE: PRT
```

<213> ORGANISM: Pertussis toxin bacteria

<400> SEQUENCE: 10

```
Lys Lys Leu Arg Arg Leu Leu Tyr Met Ile Tyr Met Ser Gly Leu Ala
1               5                   10                  15

Val Arg Val His Val Ser Lys Glu Glu Gln Tyr Tyr Asp Tyr
            20                  25                  30
```

<210> SEQ ID NO 11
<211> LENGTH: 17
<212> TYPE: PRT
<213> ORGANISM: Tetanus toxin bacteria

<400> SEQUENCE: 11

```
Lys Lys Gln Tyr Ile Lys Ala Asn Ser Lys Phe Ile Gly Ile Thr Glu
1               5                   10                  15

Leu
```

<210> SEQ ID NO 12
<211> LENGTH: 22
<212> TYPE: PRT
<213> ORGANISM: Tetanus toxin bacteria

<400> SEQUENCE: 12

```
Lys Lys Phe Asn Asn Phe Thr Val Ser Phe Trp Leu Arg Val Pro Lys
1               5                   10                  15

Val Ser Ala Ser His Leu
            20
```

<210> SEQ ID NO 13
<211> LENGTH: 15
<212> TYPE: PRT
<213> ORGANISM: Pertussis toxin bacteria

<400> SEQUENCE: 13

```
Tyr Met Ser Gly Leu Ala Val Arg Val His Val Ser Lys Glu Glu
1               5                   10                  15
```

<210> SEQ ID NO 14
<211> LENGTH: 27
<212> TYPE: PRT
<213> ORGANISM: Tetanus toxin bacteria

<400> SEQUENCE: 14

```
Tyr Asp Pro Asn Tyr Leu Arg Thr Asp Ser Asp Lys Asp Arg Phe Leu
1               5                   10                  15

Gln Thr Met Val Lys Leu Phe Asn Arg Ile Lys
            20                  25
```

<210> SEQ ID NO 15
<211> LENGTH: 24
<212> TYPE: PRT
<213> ORGANISM: Pertussis toxin bacteria

<400> SEQUENCE: 15

```
Gly Ala Tyr Ala Arg Cys Pro Asn Gly Thr Arg Ala Leu Thr Val Ala
1               5                   10                  15

Glu Leu Arg Gly Asn Ala Glu Leu
            20
```

<210> SEQ ID NO 16
<211> LENGTH: 15
<212> TYPE: PRT

-continued

```
<213> ORGANISM: Measles virus

<400> SEQUENCE: 16

Leu Ser Glu Ile Lys Gly Val Ile Val His Arg Leu Glu Gly Val
1               5                   10                  15

<210> SEQ ID NO 17
<211> LENGTH: 20
<212> TYPE: PRT
<213> ORGANISM: Measles virus

<400> SEQUENCE: 17

Gly Ile Leu Glu Ser Arg Gly Ile Lys Ala Arg Ile Thr His Val Asp
1               5                   10                  15

Thr Glu Ser Tyr
            20

<210> SEQ ID NO 18
<211> LENGTH: 16
<212> TYPE: PRT
<213> ORGANISM: Tetanus toxin bacteria

<400> SEQUENCE: 18

Trp Val Arg Asp Ile Ile Asp Asp Phe Thr Asn Glu Ser Ser Gln Lys
1               5                   10                  15

<210> SEQ ID NO 19
<211> LENGTH: 16
<212> TYPE: PRT
<213> ORGANISM: Tetanus toxin bacteria

<400> SEQUENCE: 19

Asp Val Ser Thr Ile Val Pro Tyr Ile Gly Pro Ala Leu Asn His Val
1               5                   10                  15

<210> SEQ ID NO 20
<211> LENGTH: 24
<212> TYPE: PRT
<213> ORGANISM: Chlamydia trachomitis

<400> SEQUENCE: 20

Ala Leu Asn Ile Trp Asp Arg Phe Asp Val Phe Cys Thr Leu Gly Ala
1               5                   10                  15

Thr Thr Tyr Leu Lys Glu Asn Ser
            20

<210> SEQ ID NO 21
<211> LENGTH: 23
<212> TYPE: PRT
<213> ORGANISM: Diphteria toxin bacteria

<400> SEQUENCE: 21

Asp Ser Glu Thr Ala Asp Asn Leu Glu Lys Thr Val Ala Ala Leu Ser
1               5                   10                  15

Ile Leu Pro Gly Ile Gly Cys
            20

<210> SEQ ID NO 22
<211> LENGTH: 39
<212> TYPE: PRT
<213> ORGANISM: Diphteria toxin bacteria

<400> SEQUENCE: 22

Glu Glu Ile Val Ala Gln Ser Ile Ala Leu Ser Ser Leu Met Val Ala
```

```
                1               5                  10                 15
Gln Ala Ile Pro Leu Val Gly Glu Leu Val Asp Ile Gly Phe Ala Ala
                20                 25                 30
Thr Asn Phe Val Glu Ser Cys
          35

<210> SEQ ID NO 23
<211> LENGTH: 21
<212> TYPE: PRT
<213> ORGANISM: Plasmodium falciparum

<400> SEQUENCE: 23

Asp Ile Glu Lys Lys Ile Ala Lys Met Glu Lys Ala Ser Ser Val Phe
1               5                  10                 15
Asn Val Val Asn Ser
            20

<210> SEQ ID NO 24
<211> LENGTH: 16
<212> TYPE: PRT
<213> ORGANISM: Schistoma mansoni

<400> SEQUENCE: 24

Lys Trp Phe Lys Thr Asn Ala Pro Asn Gly Val Asp Glu Lys Ile Arg
1               5                  10                 15

<210> SEQ ID NO 25
<211> LENGTH: 14
<212> TYPE: PRT
<213> ORGANISM: Escherichia coli

<400> SEQUENCE: 25

Gly Leu Gln Gly Lys Ile Ala Asp Ala Val Lys Ala Lys Gly
1               5                  10

<210> SEQ ID NO 26
<211> LENGTH: 19
<212> TYPE: PRT
<213> ORGANISM: Escherichia coli

<400> SEQUENCE: 26

Gly Leu Ala Ala Gly Leu Val Gly Met Ala Ala Asp Ala Met Val Glu
1               5                  10                 15
Asp Val Asn

<210> SEQ ID NO 27
<211> LENGTH: 20
<212> TYPE: PRT
<213> ORGANISM: Escherichia coli

<400> SEQUENCE: 27

Ser Thr Glu Thr Gly Asn Gln His His Tyr Gln Thr Arg Val Val Ser
1               5                  10                 15
Asn Ala Asn Lys
            20
```

CHIMERIC PEPTIDES AS IMMUNOGENS, ANTIBODIES THERETO, AND METHODS FOR IMMUNIZATION USING CHIMERIC PEPTIDES OR ANTIBODIES

CROSS-REFERENCE TO RELATED APPLICATIONS

The present application claims the benefit of priority under 35 U.S.C. §119(e) from U.S. provisional application No. 60/169,687, filed Dec. 8, 1999, the entire contents of which are hereby incorporated by reference.

BACKGROUND OF THE INVENTION

1. Field of the Invention

The present invention relates to a chimeric peptide immunogen containing a B cell epitope joined to a T cell epitope from a different source, immunizing compositions containing the chimeric peptide, and a method for immunization using same.

2. Description of the Background Art

A major histopathological hallmark of Alzheimer's Disease (AD) is the presence of amyloid deposits within neuritic and diffuse plaques in the parenchyma of the amygdala, hippocampus and neocortex (Glenner and Wong, 1984; Masters et al., 1985; Sisodia and Price, 1995). Amyloid is a generic term that describes fibrillar aggregates that have a common β-pleated structure. These aggregates exhibit birefringent properties in the presence of Congo red and polarized light (Glenner and Wong, 1984). The diffuse plaque is thought to be relatively benign in contrast to the neuritic plaque which appears to be strongly correlated with reactive and degenerative processes (Dickerson et al., 1988; Tagliavini et al., 1988; Yamaguchi et al., 1989; Yamaguchi et al., 1992). The principal component of neuritic plaques is a 42 amino acid residue amyloid-β (Aβ) peptide (Miller et al., 1993; Roher et al., 1993) that is derived from the much larger β-amyloid precursor protein, βAPP (or APP) (Kang et al., 1987). Two major C-terminal variants of amyloid-β peptide, Aβ 1-40 ending at Val40 and Aβ 1-42(43) ending at Ala42 or Thr43, proteolytically cleaved from βAPP, were found in amyloid deposits (Miller et al., 1993; Roher et al., 1993). Aβ 1-42 is produced less abundantly than the 1-40 Aβ peptide (Haass et al., 1992; Seubert et al., 1992), but the preferential deposition of Aβ1-42 results from the fact that this COOH-extended form is more insoluble than 1-40 Aβ and is more prone to aggregate and form anti-parallel β-pleated sheets (Joachim et al., 1989; Halverson et al., 1990; Barrow et al., 1992; Burdick et al., 1992; Fabian et al., 1994). Aβ1-42 can seed the aggregation of Aβ 1-40 (Jarrett and Lansbury 1993). Iwatsubo et al., (1996) and Saido et al., (1996) further reported that other variant amyloid-β peptides, Aβ 3(pyroglutamate)-42, Aβ 11(pyroglutamate)-42, Aβ 17-42, Aβ 1 (D-Asp)-42, and Aβ 1 (L-isoAsp)-42 were also found to be present in amyloid deposits in the brain.

The APP gene was sequenced and found to be encoded on chromosome 21 (Kang et al., 1987). Expression of the APP gene generates several Aβ-containing isoforms of 695, 751 and 770 amino acids (FIG. 1), with the latter two βAPP containing a domain that shares structural and functional homologies with Kunitz serine protease inhibitors (Kang et al., 1987; Kitaguchi et al., 1988; Ponte et al., 1988; Tanzi et al., 1988; Konig et al., 1992). The functions of βAPP in the nervous system remain to be defined, although there is increasing evidence that βAPP has a role in mediating adhesion and growth of neurons (Schubert et al., 1989; Saitoh et al., 1994; Saitoh and Roch, 1995) and possibly in a G protein-linked signal transduction pathway (Nishimoto et al., 1993). In cultured cells, βAPPs mature through the constitutive secretory pathway (Weidemann et al., 1989; Haass et al., 1992; Sisodia 1992) and some cell-surface-bound βAPPs are cleaved within the Aβ domain by an enzyme, designated α-secretase, (Esch et al., 1990), an event that precludes Aβ amyloidogenesis (FIG. 1). Several studies have delineated two additional pathways of βAPP processing that are both amyloidogenic: first an endosomal/lysosomal pathway generates a complex set of βAPP-related membrane-bound fragments, some of which contain the entire Aβ sequence (Haass et al., 1992; Golde et al., 1992); and second, by mechanisms that are not fully understood, Aβ 1-40 is secreted into the conditioned medium and is present in cerebrospinal fluid in vivo (Haass et al., 1992; Seubert et al., 1992; Shoji et al., 1992; Busciglio et al., 1993). Lysosomal degradation is no longer thought to contribute significantly to the production of Aβ (Sisodia and Price, 1995). The proteolytic enzymes responsible for the cleavages at the $NH_2$ and COOH termini of Aβ termed β and γ (FIG. 1), respectively, have not been identified. Until recently, it was generally believed that Aβ is generated by aberrant metabolism of the precursor. The presence, however, of Aβ in conditioned medium of a wide variety of cells in culture and in human cerebrospinal fluid indicate that Aβ is produced as a normal function of cells.

If amyloid deposition is a rate-limiting factor to produce AD, then all factors linked to the disease will either promote amyloid deposition or enhance the pathology that is provoked by amyloid. The likelihood of amyloid deposition is enhanced by trisomy 21 (Down's syndrome) (Neve et al., 1988; Rumble et al., 1989), where there is an extra copy of the APP gene, by increased expression of APP, and by familial Alzheimer's Disease (FAD)-linked mutations (Van Broeckhoven et al., 1987; Chartier-Harlin et al., 1991; Goate et al., 1989; Goate et al., 1991; Murrell et al., 1991; Pericak-Vance et al., 1991; Schellenberg et al., 1992; Tanzi et al., 1992; Hendricks et al., 1992; Mullan et al., 1992). Some of these mutations are correlated with an increased total production of Aβ (Cai et al., 1993; Citron et al., 1992) or specific overproduction of the more fibrillogenic peptides (Wisniewski et al., 1991; Clements et al., 1993; Suzuki et al., 1994) or increased expression of factors that induce fibril formation (Ma et al., 1994; Wisniewski et al., 1994). Collectively, these findings strongly favor the hypothesis that amyloid deposition is a critical element in the development of AD (Hardy 1992), but of course they do not preclude the possibility that other age-related changes associated with the disease, such as paired helical filaments, may develop in parallel rather than as a result of amyloid deposition and contribute to dementia independently.

The main focus of researchers and the principal aim of those associated with drug development for AD is to reduce the amount of Aβ deposits in the central nervous system (CNS). These activities fall into two general areas: factors affecting the production of Aβ, and factors affecting the formation of insoluble Aβ fibrils. A third therapeutic goal is to reduce inflammatory responses evoked by Aβ neurotoxicity.

With regards to the first, a major effort is underway to obtain a detailed understanding of how newly synthesized βAPP is processed for insertion into the plasma membrane and to identify the putative amyloidogenic secretases that have been assigned on the basis of sites for cleavage in the mature protein. From a pharmacological perspective, the most direct way of reducing the production of Aβ is through direct inhibition of either β or γ secretase. No specific inhibitors are currently available although a number of compounds have been shown to indirectly inhibit the activities. Bafilomycin, for example, inhibits Aβ production with an $EC_{50}$ of about 50 nM (Knops et al., 1995; Haass et al., 1995), most likely through its action as an inhibitor of vascular H+ATPase co-localized in vesicles with the Aβ secretase. Another compound, MDL28170, used at high concentrations appears to block the activity of γ secretase Higaki et al., 1995). It is generally hoped that the identification of the β or γ secretases might lead to the synthesis of specific protease inhibitors to block the formation of amyloidogenic peptides. It is not known, however, whether these enzymes are specific for βAPP or whether they perhaps have other important secretory functions.

Similarly, problems of target and targeting specificity will be encountered through any attempt to interfere with signal transduction pathways that may determine whether processing of βAPP is directed through the amyloidogenic or non-amyloidogenic pathways. Moreover, these signal transduction mechanisms still need to be identified. In conclusion, present understanding of the complex and varied underlying molecular mechanisms leading to overproduction of Aβ offers little hope for selective targeting by pharmacological agents.

Given that neurotoxicity appears to be associated with β-pleated aggregates of Aβ, one therapeutic approach is to inhibit or retard Aβ aggregation. The advantage of this approach is that the intracellular mechanisms triggering the overproduction of Aβ or the effects induced intracellularly by Aβ need not be well understood. Various agents that bind to Aβ are capable of inhibiting Aβ neurotoxicity in vitro, for example, the Aβ-binding dye, Congo Red, completely inhibits Aβ-induced toxicity in cultured neurons (Yankner et al., 1995). Similarly, the antibiotic rifampicin also prevents Aβ aggregation and subsequent neurotoxicity (Tomiyama et al., 1994). Other compounds are under development as inhibitors of this process either by binding Aβ directly, e.g., hexadecyl-N-methylpiperidinium (HMP) bromide (Wood et al., 1996), or by preventing the interaction of Aβ with other molecules that contribute to the formation of Aβ deposition. An example of such a molecule is heparan sulfate or the heparan sulfate proteoglycan, perlecan, which has been identified in all amyloids and is implicated in the earliest stages of inflammation associated amyloid induction.

Heparan sulfate interacts with the Aβ peptide and imparts characteristic secondary and tertiary amyloid structural features. Recently, small molecule anionic sulfates have been shown to interfere with this reaction to prevent or arrest amyloidogenesis (Kisilevsky, 1995), although it is not evident whether these compounds will enter the CNS. A peptide based on the sequence of the perlecan-binding domain appears to inhibit the interaction between Aβ and perlecan, and the ability of Aβ-derived peptides to inhibit self-polymerization is being explored as a potential lead to developing therapeutic treatments for Aβ. The effectiveness of these compounds in vitro, however, is likely to be modest for a number of reasons, most notably the need for chronic penetration of the blood brain barrier.

As another means of inhibiting or retarding Aβ aggregation, WO 96/25435 discloses the potential for using a monoclonal antibody, which is end-specific for the free C-terminus of the Aβ 1-42 peptide, but not for the Aβ 1-43 peptide, in preventing the aggregation of Aβ 1-42. While the administration of such an Aβ end-specific monoclonal antibody is further disclosed to interact with the free C-terminal residue of Aβ 1-42, thereby interfering with and disrupting aggregation that may be pathogenic in Aβ, there is no specific disclosure on how these Aβ C-terminal-specific monoclonal antibodies would be used therapeutically. Although direct or indirect manipulation of AX peptide aggregation appears to be an attractive therapeutic strategy, a possible disadvantage of this general approach may be that pharmacological compounds of this class will need to be administered over a long period of time, and may accumulate and become highly toxic in the brain tissue.

WO 98/44955 takes a novel approach to avoiding the problems associated with repeated administration of pharmacological agent and discloses a method for preventing the onset of Alzheimer's Disease or for inhibiting progression of Alzheimer's Disease through the stable ectopic expression in the brain of recombinant antibodies end-specific for amyloid-β peptides.

Recently, Schenk et al. (1999) demonstrated that immunization with amyloid-β attenuated Alzheimer's disease-like pathology in PDAPP transgenic mice serving as an animal model for amyloid-β deposition and Alzheimer's disease-like neuropathologies. They reported that immunization of young animals prior to the onset of Alzheimer's disease-type neuropathologies essentially prevented the development of β-amyloid plaque formation, neuritic dystrophy and astragliosis, whereas treatment in older animals after the onset of Alzheimer's disease-type neuropathologies was observed to reduce the extent and progression of these neuropathologies.

Although the results reported by Schenk et al. provides promise for using immunomodulation as a general approach to treat Alzheimer's disease, immunization with intact amyloid-β according to Schenk et al. has several problems that need to be addressed in developing an immunization program for treatment of Alzheimer's disease in humans. One problem is that it is not clear how readily one can raise an anti-self antibody response by immunizing humans with human amyloid-β. Moreover, even if an anti-self antibody response is raised against human amyloid-β, it is unclear whether or not auto-immunity might develop which would be injurious to the patient. Other problems include how the immunization would be reversed or halted as the antigen in the form of endogenous amyloid-β is always available to the patients' immune system and whether or not administering amyloid-β, which is believed to be neurotoxic, would have severe and adverse pharmacological effects on the patient.

An alternative to a peptide-based approach is to elucidate the cellular mechanism of Aβ neurotoxicity and develop therapeutics aimed at those cellular targets. The focus has been on controlling calcium dysfunction of free radical mediated neuronal damage. It has been postulated that Aβ binds to RAGE (the receptor for advanced glycation end-products) on the cell surface, thereby triggering reactions that could generate cytotoxic oxidizing stimuli (Yan et al., 1996). Blocking access of Aβ to the cell surface binding site(s) might retard progression of neuronal damage in Aβ. To date there are no specific pharmacological agents for blocking Aβ-induced neurotoxicity.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a chimeric peptide or mixture of chimeric peptides with an end-specific B cell epitope from a naturally-occurring internal peptide cleavage product of a precursor or mature protein, as free N-terminus or C-terminus, fused with or without spacer amino acid residue(s) to a T helper cell epitope derived from a source different from that of the internal peptide cleavage product.

The present invention also provides an immunizing composition which includes an immunizing effective amount of the chimeric peptide or mixture of chimeric peptides. This immunizing composition is used to raise antibodies in a subject mammal where the internal peptide cleavage product, for which the B cell epitope of the chimeric peptide is end-specific, is a self molecule.

Further provided by the present invention is a method for immunization of a mammal against the free N-terminus or free C-terminus of an internal self peptide cleavage product derived from a self precursor or mature protein. More particularly, the method for immunization is directed to raising antibodies and immunizing individuals against amyloid β peptides associated with amyloid β deposits and plaques.

Yet other aspects of the present invention are directed to a molecule which includes the antigen-binding portion of an antibody specific for the chimeric peptide according to the present invention and a method for passive immunization using this molecule.

DETAILED DESCRIPTION OF THE PREFERRED EMBODIMENTS

Figure 1:
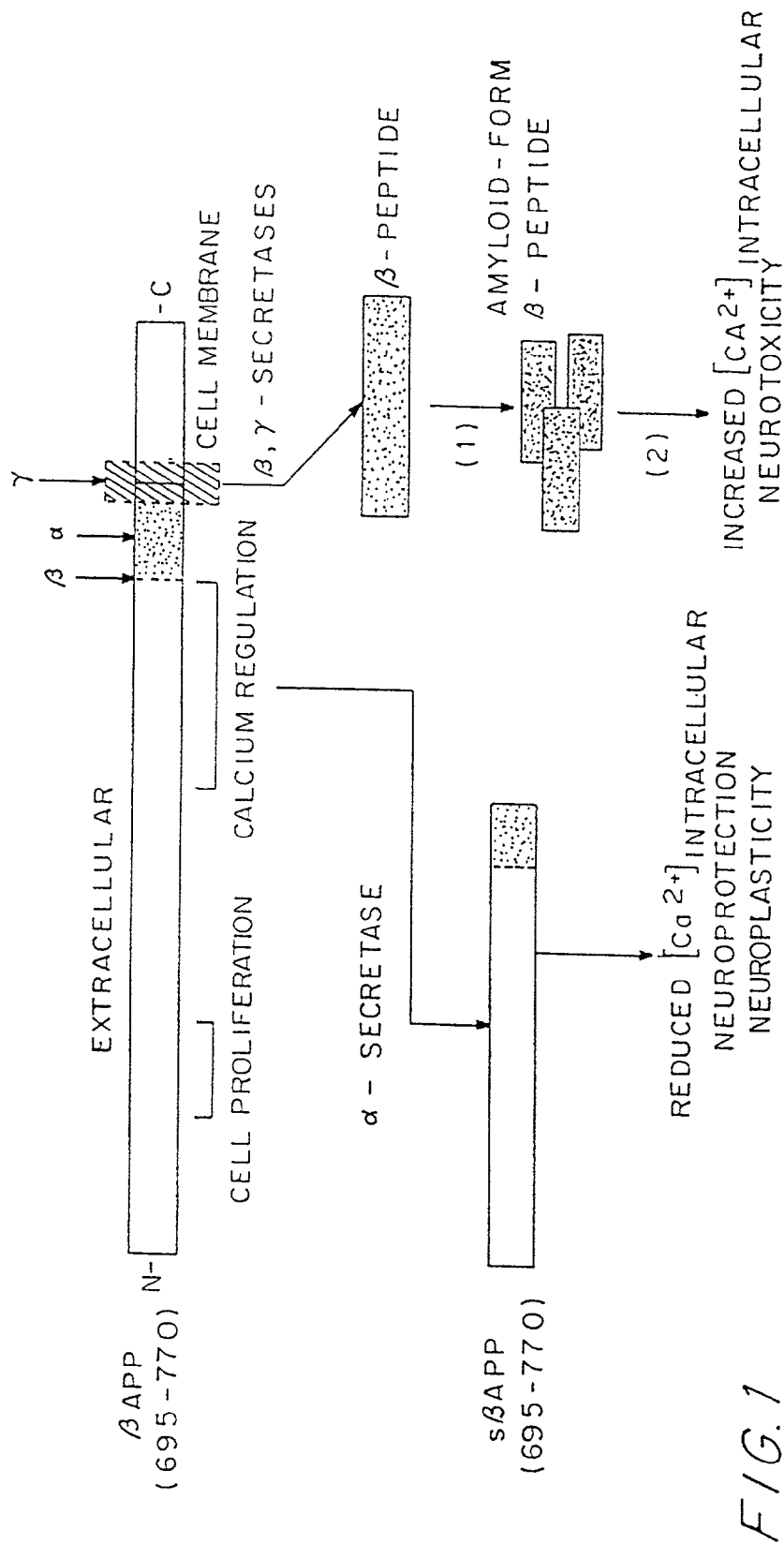
FIG. 1 shows a schematic representation of the β-amyloid precursor protein (βAPP) and the products of α, β, γ-secretase cleavage. The general locations of various domains are indicated along with the cleavage sites for α, β, and γ-secretases.
Figure 2:
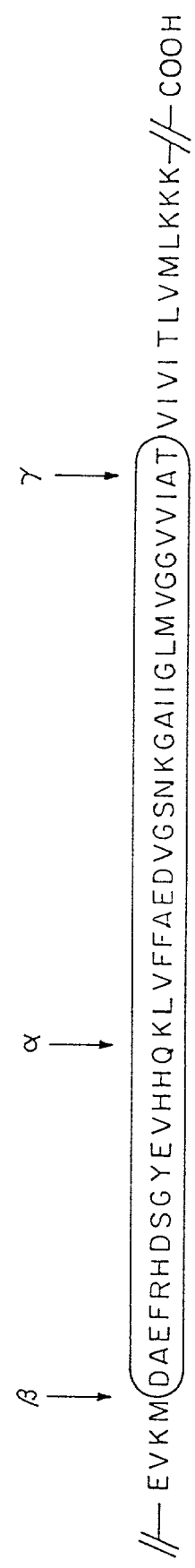
FIG. 2 shows a partial amino acid sequence (SEQ ID NO:1) of the region of βAPP from which amyloid-β peptides (As) are derived. The arrows indicate the α-, β-, and γ-secretase cleavage sites.

One aspect of the present invention is directed generally to a chimeric peptide or a mixture of chimeric peptides in which a N- or C-terminal end-specific B cell epitope from a naturally-occurring internal peptide cleavage product of a precursor or mature protein, as a free N- or C-terminus, is fused with or without spacer amino acid residue(s) to a T helper cell epitope from a different source. The chimeric peptide or peptides are used in an immunizing composition for immunizing a mammal against the free N-terminus or free C-terminus of an internal peptide cleavage product which is a self molecule of the immunized mammal (molecule native thereto). More specifically as a preferred embodiment of the present invention, the chimeric peptide(s) have an N- or C-terminal end-specific B cell epitope, which is the first two to five amino acid residues of the N-terminus or the last two to five amino acid residues of the C-terminus of an amyloid f peptide, fused to a T helper cell epitope. When such chimeric peptide(s) are administered to a human individual as part of an immunizing composition, that individual will be immunized against the amyloid β peptide or peptides from which the end-specific B cell epitope is derived.

By way of the preferred embodiments of a chimeric peptide containing an amyloid β peptide-specific B cell epitope and a method for immunizing against an amyloid β peptide as examples of the present invention, those of skill in the art will readily appreciate that the chimeric peptides(s), immunizing composition, and method for immunization can be extended and directed to other internal peptide cleavage products, for which end-specific antibodies raised by the present method would not be cross-reactive with the precursor or mature self protein. Similarly, most of the advantages described below for the method for immunization according to the present invention, which raises end-specific antibodies against amyloid β peptides in humans as a preferred embodiment, are generally applicable for immunization with the chimeric peptide or peptides of the present invention.

It is well-known that antibody responses produced by B cells to a defined region of a protein or peptide require that T helper cells of the immune system recognize another part of that antigen simultaneously. This is commonly referred to as B/T cell collaboration. According to the present invention, this phenomena can be mimicked by making a synthetic chimeric peptide which contains both B and T cell epitopes in a contiguous linear sequence. Such chimeric peptides have been used very successfully to drive antibody production in mice, human/mice chimeras and primates (Sharma et al., 1993; Ifversen et al., 1995; O'Hern et al., 1997).

In the present invention, the B cell epitope containing the first two to five amino acid residues of the free N-terminus or the last two to five amino acid residues of the free C-terminus of an amyloid β peptide is fused, with or without spacer amino acid residues, to a known strong T helper cell epitope to form a chimeric peptide. A non-limiting example of such a known strong T cell epitope is the well-studied tetanus toxoid promiscuous epitope of SEQ ID NO:B (Ho et al, 1990; Panina-Bordignon et al., 1989) as this epitope is known to work in a number of diverse human genetic backgrounds (Valmori et al., 1992 and 1994).

Immunization with the chimeric peptides(s) containing an amyloid β end-specific B cell epitope and a promiscuous T helper cell epitope of tetanus toxoid, as a preferred embodiment, should give rise to antibodies with the following specificities:

(1) anti-tetanus antibody, which would be irrelevant in humans as most individuals are already sera-positive for tetanus toxoid (i.e., from previous tetanus immunizations);

(2) anti-junction antibodies, which recognize novel epitopes created by the junction joining the end-specific B-cell epitope of an amyloid β peptide and a T helper cell epitope of tetanus toxoid, but would not recognize anything other than the immunogen itself, and therefore would be irrelevant in vivo in the immunized individual; and (3) anti-N-terminal or anti-C-terminal end-specific amyloid β antibodies, which are the desired antibodies sought to be raised by the method according to the present invention for inhibiting, reducing, or even perhaps reversing amyloid β deposit/plaque formation.

The desired anti-N-terminal or anti-C-terminal end-specific amyloid β antibodies raised by the method for immunization according to the present invention are able to discriminate between an amyloid β peptide and the β amyloid protein precursor (βAPP) from which it is proteolytically derived. These end-specific amyloid β antibodies bind specifically to the terminus/end of an amyloid β peptide to slow down, reduce or prevent the accumulation of amyloid β peptides in the extracellular space, interstitial fluid and cerebrospinal fluid of the brain, and the aggregation into senile amyloid deposits or plaques and to block the interaction of amyloid β peptides with other molecules that contribute to the neurotoxicity of amyloid β.

The presence of anti-N-terminal or anti-C-terminal end-specific amyloid β antibodies in the blood and in the extracellular space, interstitial fluid and cerebrospinal fluid of the brain, where soluble amyloid β peptides are present, promotes the formation of soluble antibody-amyloid β complexes. These soluble antibody-amyloid β complexes are cleared from the central nervous system by drainage of the extracellular space, interstitial fluid and cerebrospinal fluid into the general blood circulation through the arachnoid villi of the superior sagittal sinus. In this manner, soluble amyloid β peptides are prevented from accumulating in the extracellular space, interstitial fluid and cerebrospinal fluid to form amyloid deposits and/or to induce neurotoxicity (FIG. 1). Furthermore, clearance of soluble amyloid-β peptides in accordance with the method of the present invention is expected to reduce the inflammatory process observed in Alzheimer's Disease by inhibiting, for example, amyloid-β-induced complement activation and cytokine release, and by also blocking the interaction of Aβ with cell surface receptors such as the RAGE receptor.

As shown in FIG. 1 (see Schehr, 1994), and discussed in the Background Art section, the β-amyloid protein precursor (βAPP) is believed to also serve as a precursor for a proteolytic product, soluble β-amyloid protein precursor (sβAPP), thought to have growth promoting and neuroprotective functions. It will be readily appreciated by those of skill in the art that the anti-N-terminal or anti-C-terminal end-specific amyloid β antibodies will not interfere with the normal biological functions of βAPP that are not associated with the formation of amyloid γ peptides.

The advantages of the method for immunization according to the preferred embodiment of the present invention include:

(1) a cheap peptide antigen, that is readily and easily produced and controlled for quality assurance, is used in active immunization;

(2) inclusion of only two to three, and perhaps up to four or five, amino acid residues from the N- or C-terminus of an internal peptide cleavage product (amyloid β peptide) should minimize the amount of antibody produced which reacts with the precursor or mature protein from which the internal peptide cleavage product is proteolytically derived (βAPP), and hence might interfere with the function of this precursor or mature protein;

(3) use of an independent non-self T cell epitope should break self-tolerance and allow production of antibodies to a self-antigen (Schofield et al., 1991);

(4) the absence in the chimeric peptide(s) of a T cell epitope from the internal peptide cleavage product (amyloid β) should avoid any significant problems of autoimmunity, since anti-self T cell immunity underlies progression of all known autoimmune diseases; and (5) the immunization should be self-limiting and reversible, with antibody titers gradually falling off with time, since the patient's immune system will never naturally encounter the combination of amyloid β with tetanus toxin as immunogen. This self-limiting and reversible immunization has been demonstrated in clinical trials with synthetic contraceptive vaccines (Talwar et al., 1997).

The chimeric peptide of the present invention is represented by formula (I) or formula (II)

 (I)

 (II)

where:

N is the first 2, 3, 4 or 5 amino acid residues from the free N-terminus of a naturally-occurring internal peptide cleavage product, such as an amyloid β peptide, which, when naturally-occurring in a mammal, is derived from a precursor protein or a mature protein;

C is the last 2, 3, 4 or 5 amino acid residues from the free C-terminus of the naturally occurring internal peptide cleavage product;

$T_h$ is a T helper cell epitope derived from a natural source (i.e., species of living organism) different from that of the naturally-occurring internal peptide cleavage product S is a spacer amino acid residue;

m is 0, 1, 2, 3, 4, or 5; and n is 1, 2, 3, or 4.

Also contemplated are mixtures of chimeric peptides of formula (I) and formula (II) in which the internal peptide cleavage product of each chimeric peptide can be the same or different, i.e., different amyloid β peptides. These chimeric peptide mixtures are however not limited to mixtures of formula (I) and formula (II) chimeric peptides and can include mixtures of formula (I) peptides, where N is from different internal peptide cleavage products (i.e., different amyloid β peptides), or mixtures of formula (II) peptides, where C is from different internal peptide cleavage products (i.e., different amyloid β peptides).

The chimeric peptide of the present invention has a length between about 20 to 90 amino acid residues, preferably between about 20 to 75 amino acid residues, more preferably between about 20 to 50 amino acid residues, and most preferably between about 20 to 40 amino acid residues.

The B cell epitope from the free N-terminus (N) or the free C-terminus (C) of the naturally-occurring internal peptide cleavage product is preferably two or three amino acid residues, which is not sufficient for raising antibodies cross-reactive with the precursor protein or the mature protein of the peptide cleavage product. A B cell epitope of four or five amino acid residues from the free N-terminus or the free C-terminus of the naturally-occurring internal peptide cleavage product may also be suitable, although there is a slightly increased possibility that some antibodies may be raised which are cross-reactive with the precursor protein or the mature protein.

A preferred chimeric peptide embodiment of the present invention has a N or C in formula (I) or (II), respectively, from an amyloid β peptide which, when naturally-occurring in humans, is derived from βAPP. As used herein, the term "derived from" means that, when obtained from a natural source, the peptide or protein is the result of cleavage or conversion from a precursor protein or a mature protein, whether by a single proteolytic cleavage event or by more than one cleavage and/or conversion event. In the case of the preferred embodiment, any amyloid β peptide found to occur naturally in amyloid deposits, fibrils, and plaques is encompassed by the term "amyloid β peptide" as the internal peptide cleavage product. Peptides of SEQ ID NOs:2 (Aβ1-40), 3 (Aβ1-42), 4 (Aβ1-43), 5 (Aβ3-42), 6 (Aβ11-42), and 7 (Aβ17-42) are non-limiting examples of such "amyloid β peptides".

$T_h$ is a T helper cell epitope that is derived from a natural source different from the source of the naturally-occurring internal peptide cleavage product. In other words, the T helper cell epitope is not recognized as part of a self-molecule in the mammal subject immunized according to the method of the present invention. The T helper cell epitope is combined with a B cell epitope specific to the N-terminus or C-terminus of peptide cleavage product which is internal (not located at the ends) to a precursor or mature protein to evoke an efficient antibody response.

It is known that immunogens must be presented in conjunction with major histocompatibility (MHC) class II antigens to evoke an efficient antibody response. The MHC class II antigens produced by antigen-presenting cells (APCs) bind to T cell epitopes present in the immunogen in a sequence specific manner. This MHC class II-immunogen complex is recognized by CD4[+] lymphocytes ($T_h$ cells), which cause the proliferation of specific B cells capable of recognizing a B cell epitope from the presented immunogen and the production of B cell epitope-specific antibody by such B cells. Since amyloid β peptides are self molecules, they do not possess any recognizable $T_h$ epitopes, and B cell epitopes of 2 to 5 amino acid residues would lack any T cell epitopes altogether. Such epitopes can be provided by specific sequences derived from potent immunogens including tetanus toxin, pertussis toxin, the measles virus F protein and the hepatitis B virus surface antigen (HBsAg). The $T_h$ epitopes selected are preferably capable of eliciting T helper cell responses in large numbers of individuals expressing diverse MHC haplotypes. These epitopes function in many different individuals of a heterogeneous population and are considered to be promiscuous $T_h$ epitopes. Promiscuous $T_h$ epitopes provide an advantage of eliciting potent antibody responses in most members of genetically diverse population groups.

Moreover, the T helper cell epitopes in the chimeric peptide of the present invention are also advantageously selected not only for a capacity to cause immune responses in most members of a given population, but also for a capacity to cause memory/recall responses. When the mammal is human, the vast majority of human subjects/patients receiving immunotherapy with the chimeric peptide of the present invention will already have been immunized with the pediatric vaccines (i.e., measles+mumps+rubella and diphtheria+pertussis+tetanus vaccines) and, possibly, the hepatitis B virus vaccine. These patients have therefore been previously exposed to at least one of the $T_h$ epitopes present in chimeric pediatric vaccines. Prior exposure to a $T_h$ epitope through immunization with the standard vaccines should establish $T_h$ cell clones which can immediately proliferate upon administration of the chimeric peptide (i.e., a recall response), thereby stimulating rapid B cell responses to the chimeric peptide. In addition, the $T_h$ epitopes avoid any pathogen-specific B cell and/or suppressor T cell epitopes which could lead to carrier-induced immune suppression, a problem encountered when toxin molecules are used to elicit T helper cell responses.

The $T_h$ epitopes in the chimeric peptide of the invention are promiscuous but not universal. This characteristic means that the $T_h$ epitopes are reactive in a large segment of an outbred population expressing different MHC antigens (reactive in 50 to 90% of the population), but not in all members of that population. To provide a comprehensive, approaching universal, immune reactivity for an internal peptide cleavage product, a combination of chimeric peptides with different $T_h$ epitopes can be prepared. For example, a combination of four chimeric peptides with promiscuous $T_h$ epitopes from tetanus and pertussis toxins, measles virus F protein and HBsAg may be more effective.

Promiscuous $T_h$ epitopes often share common structural features. For example, promiscuous $T_h$ epitopes range in size from about 15 to about 30 residues. Amphipathic helices are a common feature of the $T_h$ epitopes. An amphipathic helix is defined by an α-helical structure with hydrophobic amino acid residues dominating the surrounding faces. $T_h$ epitopes frequently contain additional primary amino acid patterns such as a Gly or a charged reside followed by two to three hydrophobic residues followed in turn by a charged or polar residue. This pattern defines Rothbard sequences. $T_h$ epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single $T_h$ epitope.

$T_h$ is therefore a sequence of amino acids (natural or non-natural) that contain a $T_h$ epitope. A $T_h$ epitope can be a continuous or discontinous epitope. Hence, not every amino acid of $T_h$ is necessarily part of the epitope. Accordingly, $T_h$ epitopes, including analogs and segments of $T_h$ epitopes, are capable of enhancing or stimulating an immune response to the internal peptide cleavage product. Immunodominant $T_h$ epitopes are broadly reactive in animal and human populations with widely divergent MHC types (Celis et al., 1988; Demotz et al., 1989; and Chong et al., 1992). The $T_h$ domain of the chimeric peptides of the present invention has from about 10 to about 50 amino acids residues and preferably from about 10 to about 30 amino acids residues. When multiple $T_h$ epitopes are present (i.e., n≧2), then each $T_h$ epitope is independently the same or different.

$T_h$ epitope analogs include substitutions, deletions and insertions of one to about five amino acid residues in the $T_h$ epitope. $T_h$ segments are contiguous portions of a $T_h$ epitope that are sufficient to enhance or stimulate an immune response to the internal peptide cleavage product. An example of $T_h$ segments is a series of overlapping peptides that are derived from a single longer peptide.

The $T_h$ epitopes of the present invention include hepatitis B surface antigen T helper cell epitopes ($HB_s\ T_h$) pertussis toxin T helper cell epitopes (PT $T_h$), tetanus toxin T helper cell epitopes (TT $T_h$), measles virus F protein T helper cell epitope ($MV_{F1}\ T_h$), *Chlamydia trachomitis* major outer membrane protein T helper cell epitopes (CT $T_h$), diphtheria toxin T helper cell epitopes (DT $T_h$), *Plasmodium falciparum* circumsporozoite T helper cell epitopes (PF $T_h$), *Schistosoma mansoni* triose phosphate isomerase T helper cell epitopes (SM $T_h$), *Escherichia coli* TraT T helper cell epitopes (TraT $T_h$) and immune-enhancing analogs and epitope sequences are provided below in Table 1.

TABLE 1

| | |
|---|---|
| $TT_o\ T_h$ | SEQ ID NO: 8 |
| $HB_3\ T_h$ | SEQ ID NO: 9 |
| $TT_1\ T_h$ | SEQ ID NO: 10 |
| $TT_1\ T_h$ | SEQ ID NO: 11 |
| $TT_2\ T_h$ | SEQ ID NO: 12 |
| $PT_{L4}\ T_h$ | SEQ ID NO: 13 |
| $TT_3\ T_h$ | SEQ ID NO: 14 |
| $PT_2\ T_h$ | SEQ ID NO: 15 |
| $MV_{F1}\ T_h$ | SEQ ID NO: 16 |
| $MV_{F2}\ T_h$ | SEQ ID NO: 17 |
| $TT_4\ T_h$ | SEQ ID NO: 18 |
| $TT_5\ T_h$ | SEQ ID NO: 19 |
| $CT_1\ T_h$ | SEQ ID NO: 20 |
| $DT_1\ T_h$ | SEQ ID NO: 21 |
| $DT_2\ T_h$ | SEQ ID NO: 22 |
| PF $T_h$ | SEQ ID NO: 23 |
| SM $T_h$ | SEQ ID NO: 24 |
| $TraT_1\ T_h$ | SEQ ID NO: 25 |
| $TraT_2\ T_h$ | SEQ ID NO: 26 |
| $TraT_3\ T_h$ | SEQ ID NO: 27 |

Immunogenicity can be improved through the addition of spacer residue(s) S (i.e. Gly-Gly) between the promiscuous $T_h$ epitope and the B cell epitope of the chimeric peptide according to the present invention. In addition to physically separating the $T_h$ epitope from the B cell epitope, the glycine spacer residues can disrupt any artificial secondary structures created by the joining of the $T_h$ epitope with the B cell epitope, and thereby eliminate interference between the T and/or B cell responses. The conformational separation between the helper epitope and the antibody eliciting domain thus permits more efficient interactions between the presented immunogen and the appropriate $T_h$ and B cells. The amino acid residue(s) for S can be naturally-occurring amino acids or non-naturally-occurring amino acids, which include, but are not limited to, β-alanine, ornithine, norleucine, norvaline, hydroxyproline, thyroxine, gamma-amino butyric acid, homoserine, citrulline and the like.

The chimeric peptides of the present invention can be made by synthetic chemical methods which are well known to the ordinarily skilled artisan. Hence, the chimeric peptides can be synthesized using the automated Merrifield techniques of solid phase synthesis with either t-Boc or F-moc chemistry on Peptide Synthesizers such as an Applied Biosystems Peptide Synthesizer.

After complete assembly of the desired chimeric peptide, the resin is treated according to standard procedures to cleave the peptide from the resin and deblock the protecting groups on the amino acid side chains. The free peptide is purified by HPLC and characterized biochemically, for example, by amino acid analysis or by sequencing. Purification and characterization methods for peptides are well-known to one of ordinary skill in the art.

Alternatively, the longer linear chimeric peptides can be synthesized by well-known recombinant DNA techniques. Any standard manual on DNA technology provides detailed protocols to produce the chimeric peptides of the invention. To construct a gene encoding a chimeric peptide of the present invention, the amino acid sequence is reverse transcribed into a nucleic acid sequence, and preferably using optimized codon usage for the organism in which the gene will be expressed. Next, a synthetic gene is made, typically by synthesizing overlapping oligonucleotides which encode the peptide and any regulatory elements, if necessary. The synthetic gene is inserted in a suitable cloning vector and recombinant clones are obtained and characterized. The chimeric peptide is then expressed under suitable conditions appropriate for the selected expression system and host, and the chimeric peptide is purified and characterized by standard methods.

As an optional segment to the chimeric peptide, an immunostimulatory epitope of the invasin protein of a *Yersinia* species can be linked to the T helper cell epitope of the chimeric peptide opposite from the B cell epitope. The invasins of the pathogenic bacteria *Yersinia* spp. are outer membrane proteins which mediate entry of the bacteria into mammalian cells (Isberg et al., 1990). Invasins of cultured mammalian cells by the bacterium was demonstrated to require interaction between the *Yersinia* invasin molecule and several species of the β1 family of integrins present on the cultured cells (Tran Van Nhieu et al., 1991) Since T lymphocytes are rich in β1 integrins (especially activated immune or memory T cells) the effects of invasin on human T cell have been investigated (Brett et al., 1993). It is thought that integrins facilitate the migration of immune T cells out of the blood vessels and through connective tissues to sites of antigenic challenge through their interaction with extracellular matrix proteins including fibronectin, laminin and collagen. The carboxy-terminus of the invasin molecule was found to be co-stimulatory for naive human $CD4^+$ T in the presence of the non-specific mitogen, anti-CD3 antibody, causing marked proliferation and expression of cytokines. The specific invasin domain which interacts with the β1 integrins to cause this stimulation also was identified (Brett et al., 1993). Because of the demonstrated T cell co-stimulatory properties associated with this domain, it can be linked to the promiscuous $T_h$ epitope in the chimeric peptide of the present invention opposite from the B cell epitope.

Many of the outer membrane proteins of Gram-negative bacteria are both lipid-modified and very immunogenic. Because of the apparent correlation between covalent lipid linkage and immunogenicity, tripalmitoyl-S-glycerol cysteine ($Pam_3Cys$), a lipid common to bacterial membrane proteins, can be coupled to synthetic peptides representing either B cell or cytotoxic T cell epitopes. Because significant adjuvanting responses are elicited by this lipid linkage, promiscuous $T_h$ epitope of the chimeric peptide can be lipid modified opposite its linkage to the B cell epitope. Such lipid-modified chimeric peptides are likely to be more immunogenic than the unmodified version of the same peptide. U.S. Pat. No. 5,843,446, which includes a disclosure of $T_h$ epitopes and the immunostimulatory properties of invasin epitopes and lipid moieties, is herein incorporated entirely by reference.

Immunogenicity can further be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses, e.g. to vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and a HBsAg vaccine has been adjuvanted with alum as well.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

U.S. Pat. No. 4,855,283 teaches glycolipid analogues including N-glycosylamides, N-glycosylureas and N-glycosylcarbamates, each of which is substituted in the sugar residue by an amino acid, as immuno-modulators or adjuvants. U.S. Pat. No. 4,258,029 teaches that octadecyl tyrosine hydrochloride (OTH) functions as an adjuvant when complexed with tetanus toxoid and formalin inactived type I, II and III poliomyelitis virus vaccine. Also, Nixon-George et al., 1990, reported that octadecyl esters of aromatic amino acids complexed with a recombinant hepatitis B surface antigen enhanced the host immune responses against hepatitis B virus.

The addition of exogenous adjuvant/emulsion formulations which maximize immune responses to the internal peptide cleavage product are preferred. The adjuvants and carriers that are suitable are those: (1) which have been successfully used in Phase I human trials; (2) based upon their lack of reactogenicity in preclinical safety studies, have potential for approval for use in humans; or (3) have been approved for use in food and companion animals.

Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher co-glycolide concentrations degrade more rapidly); (2) particle size, (smaller particles degrade more rapidly than larger ones); and, (3) entrapment efficiency, (particles with higher concentrations of entrapped antigen degrade more rapidly than particle with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved. Moreover, delivery of the chimeric peptide according to the present invention entrapped in microparticles can also provide improved efficacy when the microparticulate immunogen is mixed with an exogenous adjuvant/emulsion formulations.

The efficacy of the chimeric peptides can be established and analyzed by injecting an animal, e.g., mice or rats, with the chimeric peptide formulated in alum and then following the immune response to the internal peptide cleavage product.

Another aspect of the present invention provides an immunizing composition which includes an immunizing effective amount of one or more of the chimeric peptides of the invention and a pharmaceutically acceptable carrier, excipient, diluent, or auxiliary agent, including adjuvants. Accordingly, the chimeric peptides can be formulated as an immunizing composition using adjuvants, pharmaceutically-acceptable carriers, excipients, diluents, auxiliary agents or other ingredients routinely provided in immunizing compositions. Such formulations are readily determined by one of ordinary skill in the art and include formulations for immediate release and for sustained release, e.g., microencapsulation. The present immunizing compositions can be administered by any convenient route including subcutaneous, oral, intramuscular, or other parenteral or internal route. Similarly the vaccines can be administered as a single dose or divided into multiple doses for administration. Immunization schedules are readily determined by the ordinary skilled artisan. For example, the adjuvants or emulsifiers that can be used in this invention include alum, incomplete Freund's adjuvant, liposyn, saponin, squalene, L121, emulsigen and ISA720. In preferred embodiments, the adjuvants/emulsifiers are alum, incomplete Freund's adjuvant, a combination of liposyn and saponin, a combination of squalene and L121 or a combination of emulsigned and saponin.

The immunizing compositions of the present invention contain an immunoeffective amount of one or more of the chimeric peptides and a pharmaceutically acceptable carrier. Such compositions in dosage unit form can contain about 0.5 µg to about 1 mg of each peptide per kg body weight. When delivered in multiple doses, the dosage unit form is conveniently divided into the appropriate amounts per dosage.

Immunizing compositions which contain cocktails of two or more of the chimeric peptides of the present invention enhance immunoefficacy in a broader population and thus provide a better immune response against the internal peptide cleavage product, such as amyloid β. Other immunostimulatory synthetic chimeric peptide immunogens are arrived at through modification into lipopeptides so as to provide built-in adjuvanticity for potent vaccines. The immune response to synthetic chimeric peptide immunogens of the present invention can be improved by delivery through entrapment in or on biodegradable microparticles of the type described by O'Hagan et al (1991). The immunogens can be encapsulated with or without adjuvant, including covalently attached lipid moiety such as $Pam_3Cys$, and such microparticles can be administered with an immunostimulatory adjuvant such as Freund's Incomplete Adjuvant or alum. The microparticles function to potentiate immune responses to an immunogen and to provide time-controlled release for sustained or periodic responses for oral administration, and for topical administration (O'Hagan et al., 1991).

A further aspect of the present invention is a method for immunization against the free N-terminus and/or free C-terminus of a naturally-occurring internal peptide cleavage product, which, when naturally-occurring in a mammal, is derived from a precursor protein or a mature protein. This method according to the present invention involves administering to a mammal an immunizing composition containing the chimeric peptides of the present invention for which the internal peptide cleavage product is a self molecule. A preferred embodiment of this method is one in which the method is directed to immunizing against amyloid β peptides to raise anti-N-terminal or anti-C-terminal end-specific amyloid β antibodies which do not cross-react with the β amyloid precursor protein. In this preferred embodiment, the N and/or C of formulas (I) and (II) of the chimeric peptide(s) used in the present method are from the N-terminus and/or C-terminus of amyloid β peptides.

A still further aspect of the present invention is a molecule which contains the antigen-binding portion of an antibody, preferably a monoclonal antibody, specific for the chimeric peptide according to the present invention. This molecule can be an antibody raised against the chimeric peptide in vivo or can be a recombinant antibody that is intended to encompass fragments of antibodies containing the antigen-binding portion, chimeric or humanized immunoglobulin molecules of any isotype, as well as a single-chain antibodies.

Chimeric antibodies are understood to be molecules, different portions of which are derived from different animal species, such as those humanized antibodies having a variable region derived from a mouse monoclonal antibody and a human immunoglobulin constant region. Chimeric antibodies and methods for their production are well known in the art. For example, the DNA encoding the variable region of the antibody can be inserted into or joined with DNA encoding other antibodies to produce chimeric antibodies (U.S. Pat. No. 4,816,567; Orlandi et al., 1989).

Single-chain antibodies can be single chain composite polypeptides having end-specific peptide binding capability and comprising a pair of amino acid sequences homologous or analogous to the variable regions of an immunoglobulin light and heavy chain (linked $V_H$-$V_L$ or single chain Fv). Both $V_H$ and $V_L$ may copy natural monoclonal antibody sequences, or one or both of the chains may comprise a CDR-FR construct of the type described in U.S. Pat. No. 5,091,513. The separate polypeptides analogous to the variable regions of the light and heavy chains are held together by a peptide linker. Methods of production of such single chain antibodies, e.g., single chain Fv (scFv), particularly where the DNA encoding the polypeptide structures of the $V_H$ and $V_L$ chains are characterized or can be readily ascertained by sequence analysis, may be accomplished in accordance with the methods described, for example, in U.S. Pat. Nos. 4,946,778, 5,091,513, 5,096,815, Biocca et al. (1993), Duan et al. (1994), Mhashilkar et al., (1995), Marasco et al. (1993), and Richardson et al. (1995).

Besides the conventional method of raising antibodies in vivo, antibodies can be produced in vitro using Phage Display technology. The production of recombinant antibodies is much faster compared to conventional antibody production and they can be generated against an enormous number of antigens. In contrast, in the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on Phage Display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens.

Yet another aspect of the present invention is a method for passive immunization involving administering to a mammal, preferably human, the molecule which contains the antigen-binding portion of an antibody specific for the chimeric peptide according to the present invention for which the internal peptide cleavage product is a self molecule. A preferred embodiment of this method is one in which the method is directed to passively immunizing with molecules in which the antigen-binding portion thereof is end-specific for amyloid β peptides.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Barrow et al., "Solution conformations and aggregational properties of synthetic amyloid beta-peptides of Alzheimer's disease. Analysis of circular dichroism spectra", *J. Mol. Biol.* 225:1075-1093 (1992)

Biocca et al., "Intracellular expression of anti-p21ras single chain Fv fragments inhibits meiotic maturation of xenopus oocytes", *Biochem. Biophys. Res. Commun.*, 197:422-427 (1993)

Brett et al., "The invasin protein of *Yersinia* spp. provides co-stimulatory activity to human T cells through interaction with beta 1 integrins Eur. *J. Immunol.* 23:1608-14 (1993)

Burdick et al., "Assembly and aggregation properties of synthetic Alzheimer's A4/beta amyloid peptide analogs", *J. Biol. Chem.* 267:546-564 (1992)

Busciglio et al., "Generation of beta-amyloid in the secretory pathway in neuronal and nonneuronal cells", *Proc. Natl. Acad. Sci. USA* 90:2092-2096 (1993)

Cai et al., *Science* 259:514-516 (1993)

Celis et al., "Recognition of hepatitis B surface antigen by human T lymphocytes. Proliferative and cytotoxic responses to a major antigenic determinant defined by synthetic peptides", *J. Immunol.* 140:1808-1815 (1988)

Chartier-Harlin et al., "Early-onset Alzheimer's disease caused by mutations at codon 717 of the beta-amyloid precursor protein gene", *Nature* 353:844-846 (1991)

Chong et al., "Identification of T- and B-cell epitopes of the S2 and S3 subunits of pertussis toxin by use of synthetic peptides", *Infect. Immunol.* 60:4640-4647 (1992)

Citron et al., "Excessive production of amyloid beta-protein by peripheral cells of symptomatic and presymptomatic patients carrying the Swedish familial Alzheimer disease mutation", *Proc. Natl. Acad. Sci. USA* 91:11993-11997 (1994)

Clements et al., "Effects of the mutations Glu22 to Gln and Ala21 to Gly on the aggregation of a synthetic fragment of the Alzheimer's amyloid beta/A4 peptide", *Neurosci. Lett.* 161:17-20 (1993)

Demotz et al., "Delineation of several DR-restricted tetanus toxin T cell epitopes", *J. Immunol.* 142:394-402 (1989)

Dickerson et al., *Am. J. Pathol.* 132:86-101 (1988)

Duan et al., "Potent inhibition of human immunodeficiency virus type 1 replication by an intracellular anti-Rev single-chain antibody", Proc. Natl. Acad. Sci. USA, 91:5075-5079 (1994)

Esch et al., "Cleavage of amyloid beta peptide during constitutive processing of its precursor", *Science* 248:112-1124 (1990)

Fabian et al., *Eur. J. Biochem.* 221:959-964 (1994)

Glenner et al., *Biochem. Biophys. Res. Commun.* 120:885-890 (1984)

Goate et al., *Nature* 349:704-706 (1991)

Golde et al., *Science* 255 (1992)

Grant, *Synthetic Peptides*: A User's Guide, W. H. Freeman & Co., New York, N.Y. pp. 382

Haass et al., *J. Biol. Chem.* 270:6186-6192 (1992)

Haass, C. et al., *Nature* 359:322-325 (1992).

Halverson et al., *Biochemistry* 29:2639-2664 (1990)

Hardy et al., *Science* 256:184-185 (1992)

Hendriks et al., *Nat. Genet.* 1:218-221 (1992)

Higaki et al., *Neuron* 14:651-659 (1995)

Ho et al., "Identification of two promiscuous T cell epitopes from tetanus toxin" Eur. J. Immunol. 20(3):477-83 (March 1990)

Ifversen et al., "Induction of primary antigen-specific immune responses in SCID-hu-PBL by coupled T-B epitopes" Immunology 84(1):111-6 (January 1995)

Isberg et al., *Cell* 60:861 (1990)

Iwatsubo et al., "Full-length Amyloid-β (1-42(43)) and amino-terminal modified and truncated amyloid-β 42(43) deposit in diffuse plaques", *Am. J. Pathol.* 149:1823-1830 (1996)

Jarrett et al., *Biochemistry* 32:4693-4697 (1993)

Jarrett et al., *Cell* 73:1055-1058 (1993)

Joachim et al., *Nature* 314:226-230 (1989)

Jochim et al., *Am. J. Pathol.* 135:309-319 (1989)

Kang et al., *Nature* 325:733-736 (1987)

Kiselevsky et al., *Nature Med.* 1:143-148 (1995)

Kitaguchi et al., *Nature* 331:530-532 (1988)

Knops et al., *J. Biol. Chem.* 270:2419-2422 (1995)

Konig et al., *J. Biol. Chem.* (1992)

Ma et al., *Nature* 372:92-94 (1994)

Marasco et al., *Proc. Natl. Acad. Sci. USA,* 90:7889-7893 (1993)

Masters et al., Proc. Natl. Acad. Sci. USA 82:4245-4249 (1985)

Mhashilkar et al., EMBO J., 14:1542-1551 (1995)

Miller et al., *Arch. Biochem. Biophys.* 301:41-52 (1993)

Mullan et al., *Nat. Genet.* 1:345-347 (1992)

Murrell et al., *Science* 254:97-99 (1991)

Nixon-George et al., *J. Immunology* 144:4798-4802 (1990)

Neve et al., *Neuron* 1:669-677 (1988)

O'Hagan et al., *Molec. Immunol.* 28:287-294 (1991)

O'Hagan et al., *Vaccine* 9:768-771 (1991)

O'Hern et al., "Colinear synthesis of an antigen-specific B-cell epitope with a 'promiscuous' tetanus toxin T-cell epitope: a synthetic peptide immunocontraceptive" Vaccine 15(16):176-6 (Nov. 15, 1997)

Orlandi et al., Proc Natl. Acad. Sci. USA, 86:3833-3837 (1989)

Panina-Bordignon et al., "Universally immunogenic T cell epitopes: promiscuous binding to human MHC class II and promiscuous recognition by T cells" Eur. J. Immunol. 19(12):2237-42 (December 1989)

Pericak-Vance et al., *Am. J. Genet.* 48:1034-1050 (1991)

Ponte et al., *Nature* 331:525-527 (1988)

Richardson et al., Proc. Natl. Acad. Sci. USA, 92:3137-3141 (1995)

Roher et al., *J. Neurochem.* 61:1916-1926 (1993)

Rumble et al., *N. Engl. J. Med.* 320:1446-1452 (1989)

Saido et al., "Amino-and carboxyl-terminal heterogeneity of beta-amyloid peptides deposited in human brain", *Neurosci. Lett.* 215:173-176 (1996)

Saitoh et al., "In: Amyloid Protein Precursor in Development, Aging and Alzheimer's Disease", C. L. Masters, ed. (Heidelberg, Germany, Springer-Verlag) (1994)

Schellenberg et al., *Ann. Neurol.* 31:223-227 (1992)

Schellenberg et al., *Science* 258:668-671 (1992)

Schehr, R. S., *Biotechnology* 12:140-144 (1994)

Schenk et al., "Immunization with Amyloid-β Attenuates Alzheimer Disease-like Pathology in the PDAPP Mouse", Nature 400:173-177 (1999)

Schofield et al., "Sequences of the mouse F protein alleles and identification of a T cell epitope" Eur. J. Immunol. 21(5): 1235-40 (May 1991)

Schubert et al., *Neuron* 3:689-694 (1989)

Seubert, P. et al., *Nature* 359:325-327 (1992)

Sharma et al., "Co-dominant and reciprocal T-helper cell activity of epitopic sequences and formation of junctional B-cell determinants in synthetic T:B chimeric immunogens", Vaccine 11 (13):1321-6 (October 1993)

Shoji et al., *Science* 258:126-129 (1992)

Sisodia et al., *FASEB* 9:366-370 (1995).

Sisodia et al., *Proc. Natl. Acad. Sci. USA* 89:6075-6079 (1992)

Suzuki et al., *Science* 264:1336-1340 (1994)

Tagliavini et al., *Neurosci. Lett.* 93:191-196 (1988)

Talwar et al., "The HSD-hCG vaccine prevents pregnancy in women:
feasibility study of a reversible safe contraceptive vaccine" Am. J. Reprod. Immunol. 37(2):153-60 (February 1997)

Tanzi et al., *Am. J. Hum. Genet.* 51:273-282 (1992)

Tanzi et al., *Nature* 331:528-530 (1988)

Tran Van Nhieu et al., *J. Biol. Chem.* 266:24367 (1991)

Valmori et al., "Use of human universally antigenic tetanus toxin T cell epitopes as carriers for human vaccination" J. Immunol. 149(2):717-2 (July 1992)

Valmori et al., "Functional analysis of two tetanus toxin universal T cell epitopes in their interaction with DR1101 and DR1104 alleles" J. Immunol. 152(6):2921-9 (Mar. 15, 1994)

Van Broeckhoven et al. *Nature* 329:153-155 (1987)

Weidemann et al., *Cell* 57:115-126 (1989)

Wisniewski et al., *Biochem. Biophys. Res. Commun.* 179: 1247-1254 (1991)

Wisniewski et al., *Am. J. Pathol.* 145:1030-1035 (1994)

Wood et al., *J. Biol. Chem.* 271:4086-4092 (1996)

Yamaguchi et al., *Acta Neuropathol.* 82:13-20 (1992)

Yamaguchi et al., *Am. J. Pathol.* 135:593-597 (1989)

Yan et al., *Nature* 382:685-691 (1996)

Yankner et al., *N. Eng. J. Med.* 325:1849-1857 (1991)

What is claimed is:

1. A chimeric peptide represented by formula (I) or formula (II), $$N\text{-}(S)_m\text{-}(T_h)_n \quad (I)$$

$$(T_h)_n\text{-}(S)_m\text{-}C \quad (II)$$

or chimeric peptides which are mixtures of formula (I) peptides, mixtures of formula (II) peptides, or mixtures of formula (I) and formula (II) peptides, wherein:

N is the first 2, 3, 4, or 5 amino acid residues from the free N-terminus of a naturally-occurring amyloid β peptide that is formed by proteolytic cleavage of β amyloid precursor protein (βAPP);

C is the last 2, 3, 4, or 5 amino acid residues from the free C-terminus of a naturally-occurring amyloid β peptide that is formed by proteolytic cleavage of β amyloid precursor protein (βAPP);

$T_h$ is a promiscuous T helper cell epitope;

S is a spacer amino acid residue;

m is 0, 1, 2, 3, 4, or 5; and n is 1, 2, 3, or 4.

2. The chimeric peptide or peptides according to claim 1, wherein said amyloid β peptide is selected from the group consisting of SEQ ID NOs:2, 3, 4, 5, 6, and 7.

3. The chimeric peptide or peptides according to claim 1, wherein N is the first 2 or 3 amino acid residues from the free N-terminus of said amyloid β peptide.

4. The chimeric peptide or peptides according to claim 1, wherein C is the last 2 or 3 amino acid residues from the free C-terminus of said amyloid β peptide.

5. The chimeric peptide or peptides according to claim 1, wherein said promiscuous T helper cell epitope is a T cell epitope from tetanus toxin, pertussis toxin, diphtheria toxin, measles virus F protein, hepatitis B virus surface antigen, *Chlamydia trachomitis* major outer membrane protein, *Plasmodium falciparum* circumsporozoite, *Schistosoma mansoni* triose phosphate isomerase, or *Escherichia coli* TraT.

6. The chimeric peptide or peptides according to claim 5, wherein said promiscuous T helper cell epitope has an amino acid sequence selected from the group consisting of SEQ ID NOs: 8 to 27.

7. The chimeric peptide or peptides according to claim 1, wherein S is glycine.

8. An immunizing composition, comprising an immunizing effective amount of the chimeric peptide or peptides according to claim 1 and a pharmaceutically acceptable carrier, excipient, diluent, or auxiliary agent.

9. The immunizing composition according to claim 8, wherein said pharmaceutically acceptable auxiliary agent is an adjuvant.

10. The immunizing composition according to claim 9, wherein said adjuvant is alum.

11. A method for immunization against a free N-terminus or free C-terminus of an amyloid β peptide, comprising administering to a mammal the immunizing composition according to claim 8, for which the amyloid β peptide is a self molecule of the mammal.

12. The method according to claim 11, wherein the mammal is a human.

13. A chimeric peptide of formula (I) or formula (II), $$N\text{-}(S)_m\text{-}(Th)_n \quad (I)$$

$$(Th)_n\text{-}(S)_m\text{-}C \quad (II)$$

or chimeric peptides which are mixtures of formula (I) peptides, mixtures of formula (II) peptides, or mixtures of formula (I) and formula (II) peptides, wherein:

N is the first 2, 3, or 4 amino acid residues from the free N-terminus of a naturally-occurring internal amyloid β peptide cleavage product that is formed by proteolytic cleavage of an amyloid precursor protein;

C is the last 2, 3, or 4 amino acid residues from the free C-terminus of a naturally-occurring internal amyloid β peptide cleavage product, that is formed by proteolytic cleavage of an amyloid precursor protein;

$T_h$ is a promiscuous T helper cell epitope;

S is a spacer amino acid residue;

m is 0, 1, 2, 3, 4, or 5; and n is 1, 2, 3, or 4.

14. The chimeric peptide or peptides according to claim 13, wherein m is 1, 2, 3, 4 or 5.

15. The chimeric peptide or peptides according to claim 13, wherein said internal amyloid β peptide cleavage product has an amino acid sequence selected from the group consisting of SEQ ID NOs: 2, 3, 4, 5, 6, and 7.

16. The chimeric peptide or peptides according to claim 13, wherein said promiscuous T helper cell epitope is a T cell epitope from tetanus toxin, pertussis toxin, diphtheria toxin, measles virus F protein, hepatitis B virus surface antigen, *Chlamydia trachomitis* major outer membrane protein, *Plasmodium falciparum* circumsporozoite, *Schistosoma mansoni* triose phosphate isomerase, or *Escherichia coli* TraT.

17. The chimeric peptide or peptides according to claim 16, wherein N is the first 2 or 3 amino acid residues from the free N-terminus of said internal amyloid β peptide cleavage product.

18. The chimeric peptide or peptides according to claim 16, wherein C is the last 2 or 3 amino acid residues from the free C-terminus of said internal amyloid β peptide cleavage product.

19. The chimeric peptide or peptides according to claim 16, wherein said promiscuous T helper cell epitope has an amino acid sequence selected from the group consisting of SEQ ID NOs: 8 to 27.

20. The chimeric peptide or peptides according to claim 13, wherein S is glycine.

21. An immunizing composition, comprising an immunizing effective amount of the chimeric peptide or peptides according to claim 13 and a pharmaceutically acceptable carrier, excipient, diluent, or auxiliary agent.

22. The immunizing composition according to claim 21, wherein said pharmaceutically acceptable auxiliary agent is an adjuvant.

23. The immunizing composition according to claim 22, wherein said adjuvant is alum.

24. A method for immunization against the free N-terminus or free C-terminus of an amyloid β peptide, comprising administering to a mammal the immunizing composition according to claim 21, for which the amyloid β peptide is a self molecule of the mammal.

25. The method according to claim 24, wherein the mammal is a human.

\* \* \* \* \*